US00PP20546P2

(12) United States Plant Patent
Bergman

(10) Patent No.: US PP20,546 P2
(45) Date of Patent: Dec. 8, 2009

(54) ***CHRYSANTHEMUM* PLANT NAMED 'YOPUEBLO'**

(50) Latin Name: *Chrysanthemum×morifolium*
Varietal Denomination: Yopueblo

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/283,273

(22) Filed: Sep. 8, 2008

(51) Int. Cl.
*A01H 5/00* (2006.01)

(52) U.S. Cl. ..... Plt./296

(58) Field of Classification Search ..... Plt./296
See application file for complete search history.

(56) References Cited

U.S. PATENT DOCUMENTS

PP12,526 P2 * 4/2002 Vandenberg et al. ..... Plt./296

OTHER PUBLICATIONS

Plant Varieties Journal No. 68 Jul. 2008 (112 pages) See Esp. p. 13.*

* cited by examiner

*Primary Examiner*—Wendy C. Haas
(74) *Attorney, Agent, or Firm*—C. A. Whealy

(57) ABSTRACT

A new and distinct cultivar of *Chrysanthemum* plant named 'Yopueblo', characterized by its upright, outwardly spreading and uniformly mounded plant habit; moderately vigorous growth habit; freely branching habit; dark green-colored foliage; uniform, freely and early flowering habit; daisy-type inflorescences with orange bronze-colored ray florets and green-colored disc florets; and excellent postproduction longevity.

1 Drawing Sheet

Botanical designation: *Chrysanthemum×morifolium.*
Cultivar denomination: 'Yopueblo'.

BACKGROUND OF THE INVENTION

The present invention relates to a new and distinct cultivar of *Chrysanthemum* plant, botanically known as *Chrysanthemum×morifolium*, commercially grown as a pot-type *Chrysanthemum* and hereinafter referred to by the name 'Yopueblo'.

The new *Chrysanthemum* is a product of a breeding program conducted by the Inventor in Fort Myers, Fla. The objective of the breeding program is to create new pot-type *Chrysanthemum* cultivars that are suitable for year-round production with uniform plant growth habit, freely branching habit, good vigor, desirable inflorescence form and floret colors, fast response time and excellent postproduction longevity.

The new *Chrysanthemum* originated from a cross-pollination made by the Inventor in January, 2004, in Salinas, Calif. of a proprietary selection of *Chrysanthemum×morifolium* identified as code number YB-A4929, not patented, as the female, or seed, parent with a proprietary selection of *Chrysanthemum×morifolium* identified as code number YB-A3803, not patented, as the male, or pollen, parent. The new *Chrysanthemum* was discovered and selected by the Inventor as a single flowering plant within the progeny of the stated cross-pollination in a controlled greenhouse environment in Fort Myers, Fla. in March, 2005.

Asexual reproduction of the new *Chrysanthemum* by vegetative tip cuttings was first conducted in a controlled greenhouse environment in Fort Myers, Fla. in June, 2005. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yopueblo'. These characteristics in combination distinguish 'Yopueblo' as a new and distinct pot-type *Chrysanthemum* cultivar:

1. Compact, upright, outwardly spreading and uniformly mounded plant habit.
2. Moderately vigorous growth habit.
3. Freely branching habit.
4. Dark green-colored foliage.
5. Uniform, freely and early flowering habit.
6. Daisy-type inflorescences with orange bronze-colored ray florets and green-colored disc florets.
7. Excellent postproduction longevity with inflorescences maintaining good substance and color for about four to five weeks in an interior environment.

Plants of the new *Chrysanthemum* differ from plants of the female parent selection primarily in plant habit as plants of the *Chrysanthemum* are more upright than plants of the female parent selection. In addition, plants of the new *Chrysanthemum* have stronger stems than plants of the female parent selection.

Plants of the new *Chrysanthemum* differ from plants of the male parent selection in the following characteristics:

1. Plants of the new *Chrysanthemum* are shorter than plants of the male parent selection.
2. Plants of the new *Chrysanthemum* and the male parent selection differ in ray floret color as plants of the male parent selection have red-colored ray florets.

3. Plants of the new *Chrysanthemum* do not produce pollen whereas plants of the male parent selection produce pollen.

Plants of the new *Chrysanthemum* can be compared to plants of *Chrysanthemum×morifolium* 'Yoauburn', disclosed in U.S. Plant Pat. No. 12,526. In side-by-side comparisons conducted in Fort Myers, Fla., plants of the new *Chrysanthemum* primarily from plants of 'Yoauburn' in the following characteristics:

1. Inflorescences of pants of the new *Chrysanthemum* had a larger disc than inflorescences of plants of 'Yoauburn'.
2. Plants of the new *Chrysanthemum* and 'Yoauburn' differed in disc floret color as plants of 'Yoauburn' had bright yellow-colored disc florets.
3. Plants of the new *Chrysanthemum* and 'Yoauburn' differed slightly in ray floret color as plants of 'Yoauburn' had ray florets that were tinged with red.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of typical flowering plants of 'Yopueblo' grown in a container.

The photograph at the top of the sheet is a close-up view of typical inflorescences of 'Yopueblo'.

DETAILED BOTANICAL DESCRIPTION

The aforementioned photographs and following observations and measurements describe plants grown in Leamington, Ontario, Canada during the late spring in a glass-covered greenhouse and under conditions and practices which approximate those generally used in commercial pot-type *Chrysanthemum* production. During the production of the plants, day temperatures ranged from 20° C. to 24° C., night temperatures ranged from 15° C. to 17° C. and light levels ranged from 4,000 to 6,000 foot candles. Four unrooted cuttings were directly stuck in 15-containers, exposed to long day/short night conditions, and pinched about two weeks later. One week after the pinch, the photoinductive short day/long night treatments were started. Plants used in the photographs and for the description had been growing for eleven weeks and were grown as spray-types. In the following description, color references are made to The Royal Horticultural Society Colour Chart, 2001 Edition, except where general terms of ordinary dictionary significance are used.

Botanical classification: *Chrysanthemum×morifolium* 'Yopueblo'.

Parentage:

*Female, or seed, parent.*—Proprietary selection of *Chrysanthemum×morifolium* identified as code No. YB-A4929, not patented.

*Male, or pollen, parent.*—Proprietary selection of *Chrysanthemum×morifolium* identified as code No. YB-A3803, not patented.

Propagation:

*Type.*—Terminal vegetative cuttings.

*Time to initiate roots.*—About four days at temperatures of 21° C.

*Time to produce a rooted young plant.*—About ten days at temperatures of 21° C.

*Root description.*—Fine to thick, fibrous; white in color.

*Rooting habit.*—Freely branching; moderately dense.

Plant description:

*Appearance.*—Herbaceous daisy pot-type *Chrysanthemum* typically grown as a natural spray type. Compact; stems upright and outwardly spreading giving a uniformly mounded appearance to the plant. Freely branching habit, about seven lateral branches develop after removal of terminal apex (pinching); dense and full plant habit. Moderately vigorous growth habit.

*Plant height.*—About 26 cm.

*Plant width.*—About 23 cm.

*Lateral branches.*—Length: About 23 cm. Diameter: About 4 mm. Internode length: About 2.3 cm. Strength: Strong. Texture: Pubescent; longitudinally ridged. Color: Close to 146C.

Foliage description:

*Arrangement.*—Alternate, simple.

*Length.*—About 8.4 cm.

*Width.*—About 5 cm.

*Shape.*—Palmately lobed.

*Apex.*—Cuspidate.

*Base.*—Attenuate.

*Margin.*—Palmately lobed, sinuses between lateral lobes parallel.

*Texture, upper and lower surfaces.*—Fine pubescence; veins prominent on lower surface.

*Color.*—Developing leaves, upper surface: Close to N137A. Developing leaves, lower surface: Close to 147B. Fully expanded leaves, upper surface: Close to 147A; venation, close to 147B. Fully expanded leaves, lower surface: Close to 147B; venation, close to 147B.

*Petiole.*—Length: About 1.5 cm. Diameter: About 3 mm. Texture, upper and lower surfaces: Pubescent. Color, upper and lower surfaces: Close to 146B.

Inflorescence description:

*Appearance.*—Daisy-type inflorescence form with elongated oblong-shaped ray florets. Inflorescences borne on terminals above foliage. Disc and ray florets arranged acropetally on a capitulum. Typically grown as a spray-type.

*Fragrance.*—Faint; spicy, herbaceous.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to two weeks of long day/short night conditions followed by photoinductive short day/long night conditions flower about eight weeks later.

*Postproduction longevity.*—Inflorescences maintain good color and substance for about four to five weeks in an interior environment; inflorescences persistent.

*Quantity of inflorescences.*—Freely flowering, about four to six inflorescences develop per lateral stem.

*Inflorescence bud.*—Height: About 1.6 cm. Diameter: About 1.8 cm. Shape: Oblate. Color: Close to 161A.

*Inflorescence size.*—Diameter: About 7.3 cm. Depth (height): About 2 cm. Diameter of disc: About 1.3 cm. Receptacle height: About 5 mm. Receptacle diameter: About 2 cm. Receptacle color: Close to 147B.

*Ray florets.*—Shape: Elongated oblong. Orientation: Initially upright, with development, perpendicular to the peduncle. Aspect: Mostly flat. Length: About 3.4 cm. Width: About 1 cm. Apex: Rounded to slightly emarginate. Base: Attenuate; short corolla tube. Margin: Entire. Texture, upper and lower surfaces: Smooth, glabrous; velvety. Number of ray florets per inflorescence: About 30 arranged in about two to three whorls. Color: When opening, upper surface: Close to 163A. When opening, lower surface: Close to 163C. Fully opened, upper surface: Close to 163B; towards the base, close to 7A; color does not fade with development. Fully opened, lower surface: Close to 163D; color does not fade with development.

*Disc florets.*—Arrangement: Massed at center of receptacle. Shape: Tubular, elongated. Apex: Five-pointed. Length: About 8 mm. Diameter: About 2 mm. Number of disc florets per inflorescence: About 211. Color, immature: Apex: Close to 151B. Mid-section: Close to 12A. Base: Close to 145D. Color, mature: Apex: Close to 12B. Mid-section: Close to 145C. Base: Close to 145D.

*Phyllaries.*—Number of phyllaries per inflorescence: About 30 arranged in about two whorls. Length: About 7 mm. Width: About 4 mm. Shape: Narrowly elliptical. Apex: Acute. Base: Truncate. Margin: Entire. Texture, upper surface: Smooth, glabrous; waxy. Texture, lower surface: Pubescent. Color, upper surface: Close to 146A. Color, lower surface: Close to N137B.

*Peduncles.*—Length: About 8.8 cm. Diameter: About 2 mm. Angle: About 45° from vertical. Strength: Strong, flexible. Texture: Pubescent. Color: Close to 147B.

*Reproductive organs.*—Androecium: Present on disc florets only. Filament length: About 3 mm. Filament color: Close to 150C. Anther shape: Oblong. Anther length: About 3.5 mm. Anther color: Close to 14A. Pollen amount: None observed. Gynoecium: Present on both ray and disc florets. Pistil length: About 8 mm. Stigma shape: Bi-parted. Stigma color: Close to 13B. Style length: About 4 mm. Style color: Close to 1B. Ovary color: Close to 155D.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* tolerate temperatures ranging from about 5° C. to about 38° C.

It is claimed:

1. A new and distinct *Chrysanthemum* plant named 'Yopueblo' as illustrated and described.

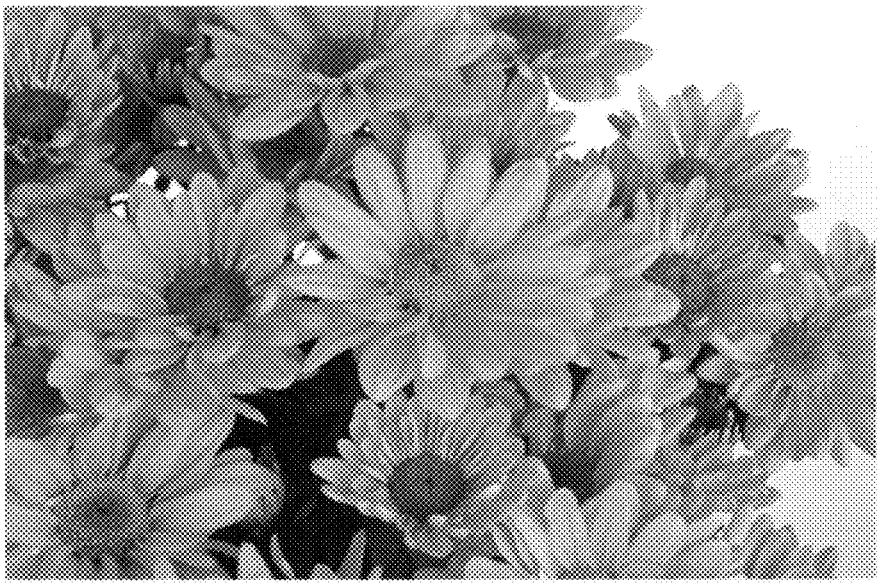
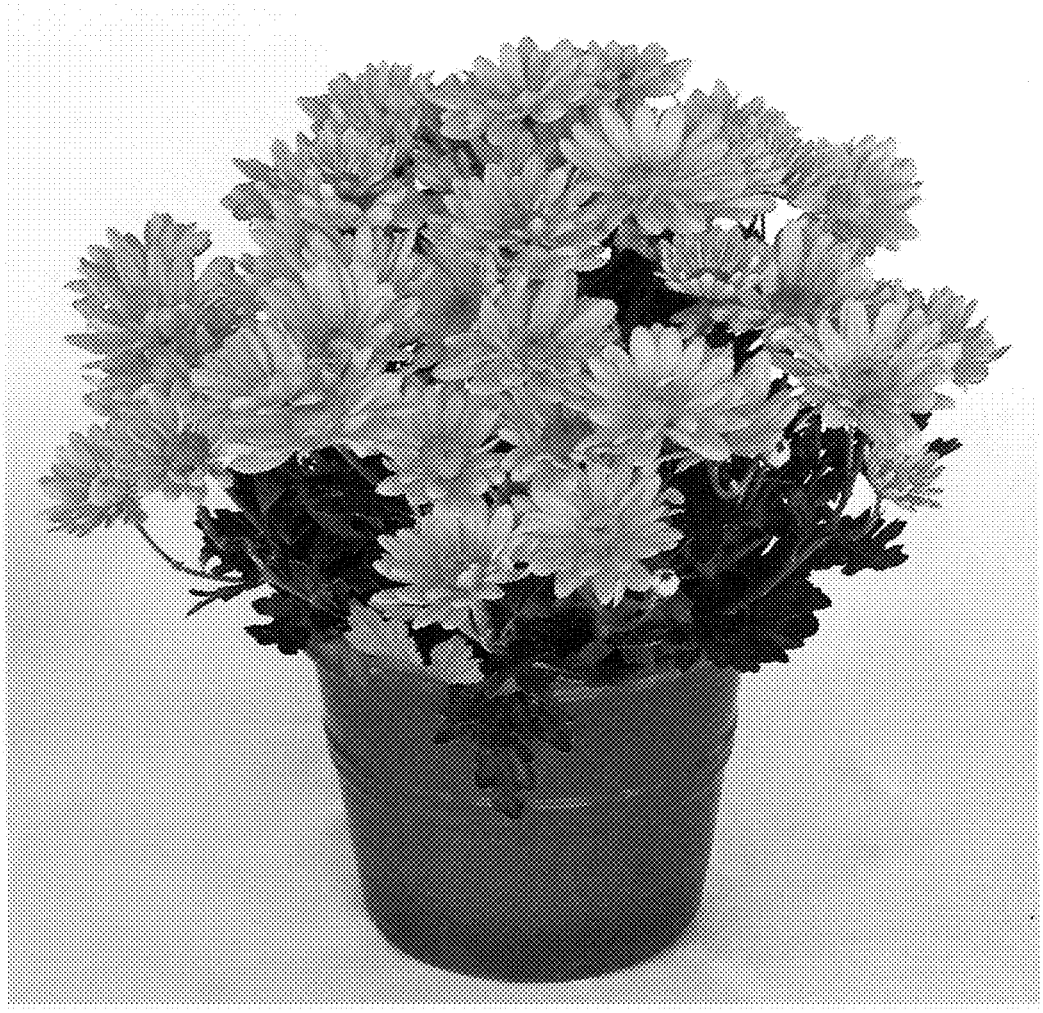

* * * * *